United States Patent
Soltermann et al.

(10) Patent No.: US 12,209,002 B2
(45) Date of Patent: Jan. 28, 2025

(54) NESTED LIFTING COLUMNS

(71) Applicant: Ewellix AB, Gothenburg (SE)

(72) Inventors: Marcel Soltermann, Liestal (CH);
Martin Voegelin, Liestal (CH);
Emmanuel Eyraud, Liestal (CH);
Daniel Greilinger, Liestal (CH)

(73) Assignee: Ewellix AB, Goeteborg (SE)

( * ) Notice: Subject to any disclaimer, the term of this patent is extended or adjusted under 35 U.S.C. 154(b) by 0 days.

(21) Appl. No.: 18/302,146

(22) Filed: Apr. 18, 2023

(65) Prior Publication Data

US 2023/0373766 A1    Nov. 23, 2023

(30) Foreign Application Priority Data

May 17, 2022   (DE) ..................... 10 2022 112 279.4

(51) Int. Cl.
| | |
|---|---|
| *B66F 3/10* | (2006.01) |
| *B66F 3/18* | (2006.01) |
| *B66F 3/44* | (2006.01) |
| *F16H 25/20* | (2006.01) |

(52) U.S. Cl.
CPC .................. *B66F 3/10* (2013.01); *B66F 3/18* (2013.01); *B66F 3/44* (2013.01); *B66F 2700/04* (2013.01); *F16H 2025/2059* (2013.01)

(58) Field of Classification Search
CPC .......... B66F 3/10; B66F 3/18; B66F 2700/04; B66F 9/205; F16H 2025/2059; A61G 13/06
See application file for complete search history.

(56) References Cited

U.S. PATENT DOCUMENTS

| | | | | |
|---|---|---|---|---|
| 3,902,070 | A * | 8/1975 | Amor, Jr. ................. | B23Q 5/58 378/197 |
| 7,458,562 | B1 * | 12/2008 | Chen ......................... | B66F 3/10 254/2 B |
| 2009/0021092 | A1* | 1/2009 | Elliott ...................... | B64C 25/30 310/83 |
| 2014/0007348 | A1* | 1/2014 | Greilinger .............. | A61G 13/02 5/611 |
| 2015/0075306 | A1* | 3/2015 | Castelli ................... | F16H 25/20 74/89.35 |
| 2015/0102201 | A1* | 4/2015 | Aoyagi ................... | F16M 11/18 248/615 |
| 2018/0314053 | A1* | 11/2018 | Jakober .................. | F16M 11/28 |
| 2020/0148516 | A1* | 5/2020 | Greilinger ............ | A61B 6/4405 |
| 2022/0348444 | A1* | 11/2022 | Hu ......................... | E04H 12/182 |

FOREIGN PATENT DOCUMENTS

| | | |
|---|---|---|
| CN | 202690627 U | 1/2013 |
| DE | 202017102534 U1 | 6/2017 |

* cited by examiner

*Primary Examiner* — Charles A Fox
*Assistant Examiner* — Gregory T Prather
(74) *Attorney, Agent, or Firm* — Laurence A. Greenberg; Werner H. Stemer; Ralph E. Locher

(57) ABSTRACT

A lifting column includes at least five column elements which are at least partly nested, and a first and a second drive arrangement. The first drive arrangement is configured to move the three innermost column elements relative to one another. The second drive arrangement is configured to move the three outermost column elements relative to one another.

15 Claims, 3 Drawing Sheets

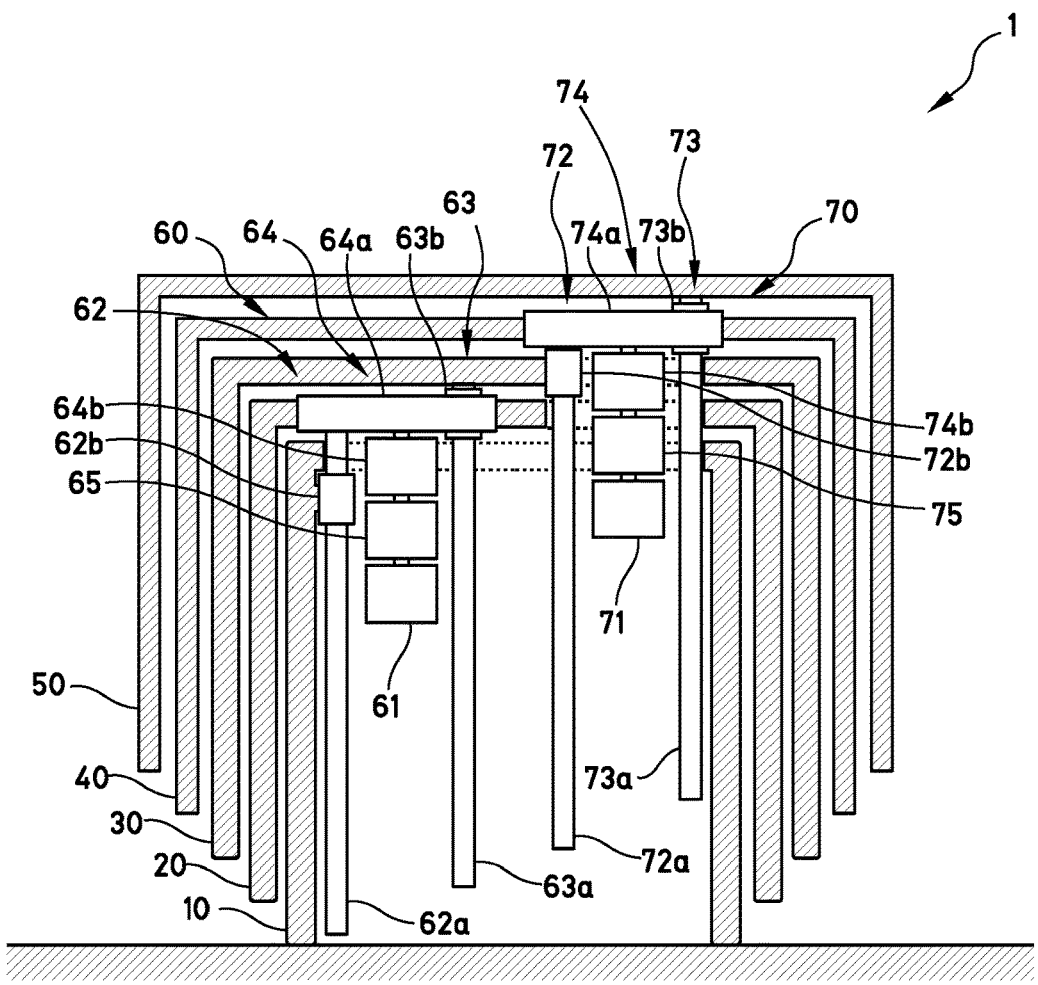
Fig. 1
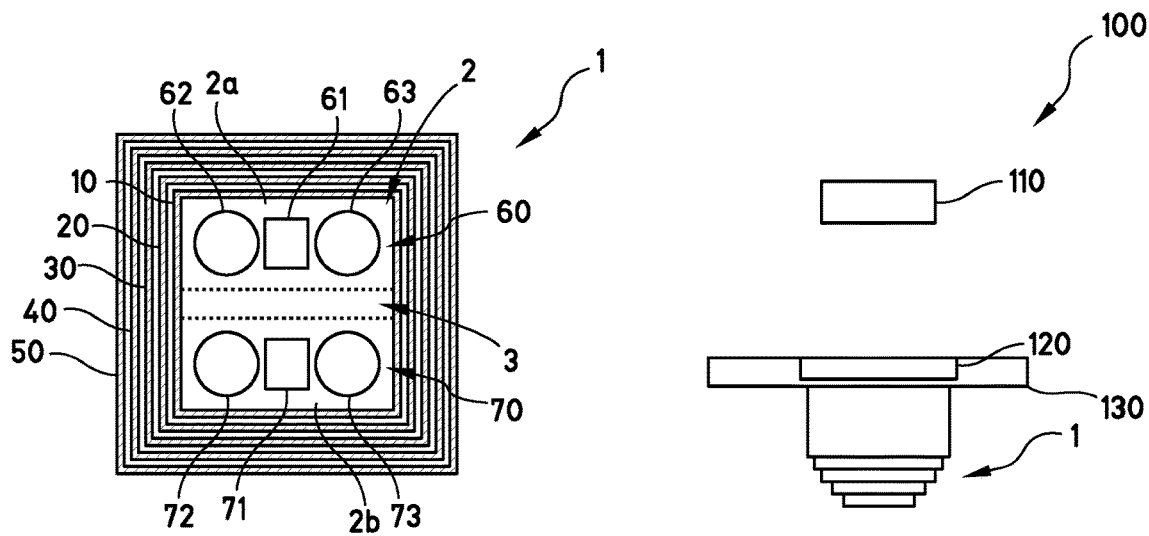
Fig. 3
Fig. 6

NESTED LIFTING COLUMNS

CROSS-REFERENCE TO RELATED APPLICATION

This application claims the priority, under 35 U.S.C. § 119, of German Patent Application DE 10 2022 112 279.4, filed May 17, 2022; the prior application is herewith incorporated by reference in its entirety.

FIELD AND BACKGROUND OF THE INVENTION

The invention concerns a lifting column.

For lifting loads, lifting columns are known which usually comprise two or more column elements arranged in nested fashion. In order to telescope the lifting column, i.e. move the column elements relative to one another, usually a motor is arranged in the interior of the lifting column. In most lifting columns, this motor drives a screw gear with a threaded spindle and a spindle nut. The extension of the lifting column is here limited by the travel of the spindle nut on the threaded spindle. To extend the travel, cable pull systems coupled to the screw gear are known.

SUMMARY OF THE INVENTION

It is an object of the invention to indicate an improved lifting column. In particular, it is an object of the invention to indicate a lifting column which has a greater extension and is stable both under pressure and tension.

This object is achieved by a lifting column according to the independent claim.

Preferred embodiments are the subject of the dependent claims and the following description.

A first aspect of the invention concerns a lifting column with at least five column elements which are at least partly nested, and a first and a second drive arrangement. The first drive arrangement is configured to move the three innermost column elements. The second drive arrangement is configured to move the three outermost column elements relative to one another.

The invention is based on the concept of equipping a lifting column with at least five nested column elements and two drive arrangements, wherein the drive arrangements suitably work in complementary fashion. In other words, a first drive arrangement can move the three innermost of the five column elements, and a second drive arrangement can move the three outermost of the five column elements relative to one another. It is thereby possible to increase the extension in comparison with conventional lifting columns, or at least achieve a comparable extension with significantly more robust design. In particular, because of the two drive arrangements, it is possible to move the lifting column portions optionally in synchrony or independently of one another.

For this, the column elements suitably lie at least in part inside one another and/or are arranged movably relative to one another. In other words, the five column elements are suitably configured and arranged such that the lifting column is telescopic. For example, a fourth column element may be arranged at least in part in a fifth column element, a third column element at least in part in the fourth column element, a second column element at least in part in the third column element, and a first column element at least in part in the second column element.

Preferred embodiments of the invention and their refinements are described below, each of which, unless expressly excluded, may be arbitrarily combined together or with the aspects of the invention described below.

In a preferred embodiment, the first and second drive arrangements are mechanically coupled together via the middle, i.e. the third, column element. Thus the extension achieved by means of the second drive arrangement may be added to the extension achieved by means of the first drive arrangement. The extension may thus be particularly large. Thus an upper part of the lifting column, for example the three outermost column elements, or the third, fourth and fifth column elements, may be moved independently of a lower part of the lifting column, for example the three innermost column elements, or the first, second and third column elements.

In a further preferred embodiment, the first and second drive arrangements are arranged laterally offset to one another. A lateral offset may here be in particular an offset transversely to a longitudinal axis of the lifting column or column elements, or e.g. also diagonally across the corners of the lifting columns. Depending on the extension of the lifting column, the two drive arrangements can thus at least in part be arranged laterally next to one another.

For example, the two drive arrangements may each be arranged in a half of the interior of the lifting column. A half of the interior is here suitably a half defined by a longitudinal section. Thus in the retracted state, the lifting column may be axially particularly compact.

In a further preferred embodiment, each of the drive arrangements comprises a drive, for example a motor. With corresponding control, the lifting column portions can thus be moved independently of one another if required, e.g. on a failure of one of the drives.

Suitably, each of the drive arrangements also comprises two screw gears actively connected to the (respective) drive, each with a threaded spindle and a spindle nut. In comparison with merely a single driven screw gear, thus a fourfold extension can be achieved. The use of screw gears also allows a direct and efficient conversion of a drive torque into a movement of the column elements. In contrast to lifting columns with e.g. a telescopic threaded spindle or cable pull system, the desired extension of the lifting column can be achieved more precisely.

Here, the use of widely varying designs of screw gears, which may sometimes be described as spindle drives, is conceivable. For example, the (total of four) screw gears may be configured as pure spindle-nut systems in which the spindle nut sits directly on the threaded spindle. It is however also conceivable that the screw gears are designed as ball or roller thread drives, or even as planetary roller thread drives.

Suitably, each of the drives is configured for driving the threaded spindle of one of the two screw gears actively connected thereto and for driving the spindle nut of the other of the two screw gears connected thereto. In other words, each drive preferably drives a threaded spindle of the one screw gear and a spindle nut of the other screw gear. To this extent, suitably a respective threaded spindle and spindle nut may be axially or translationally fixed relative to the drives and rotatable by means of the drives. Thus the installation space in the lifting column may be utilized efficiently.

A particularly compact arrangement and/or efficient torque transmission may be achieved if each of the two drives has a drive shaft which is actively connected via a gear mechanism to the screw gears of the respective drive arrangement. Alternatively or additionally to a gear mechanism for torque adaptation or optimization, here in particular it is conceivable for the gear mechanism to be formed as a so-called flat gear in which for example gearwheels are arranged intermeshing in one plane. Thus the drives may be reliably actively connected to the respective screw gears even if the screw gears are arranged laterally offset to the respective drive shaft. In other words, by means of the gear mechanism, torque can be transmitted from the drive shafts to the screw gears even if the rotational axes of the threaded spindles and/or spindle nuts run parallel but laterally offset to the rotational axis of the drive shafts.

Similarly, with a view to a compact arrangement, it is advantageous if the drive of the first drive arrangement is fixed to the middle one of the three innermost column elements. In other words, the drive of the first drive arrangement may be fixed to the second column element in order to move this relative to the first column element by means of a screw gear driven thereby, and relative to the third column element by means of the other screw gear driven thereby.

To this extent, it is suitable if one of the two threaded spindles and one of the two spindle nuts of the first drive arrangement are mounted rotatably on the middle one of the three innermost column elements, i.e. in particular on the second column element. Accordingly, the other of the two threaded spindles of the first drive arrangement is preferably fixed to the middle one of the five column elements, i.e. in particular the third column element, while the other of the two spindle nuts of the first drive arrangement is fixed to the innermost column element, i.e. in particular the first column element. Thus the threaded spindle, which is rotatably mounted (and driven) on the second column element, can turn up the corresponding spindle nut—and hence also the second column element on the first (innermost) column element—while the spindle nut, which is rotatably mounted (and driven) on the second column element, can push up the corresponding threaded spindle—and hence the third (middle) column element relative to the second column element.

Alternatively or additionally, with a view to a compact arrangement, it is advantageous if the drive of the second drive arrangement is fixed on the middle one of the three outermost column elements. In other words, the drive of the second drive arrangement may be fixed to the fourth column element in order to move this relative to the third column element by means of the one screw gear driven thereby, and relative to the fifth column element by means of the other screw gear driven thereby.

To this extent, it is suitable if one of the two threaded spindles and one of the two spindle nuts of the second drive arrangement are mounted rotatably on the middle one of the three outermost column elements, i.e. in particular on the fourth column element. Accordingly, the other of the two threaded spindles of the second drive arrangement is preferably fixed to the outermost column element, i.e. in particular the fifth column element, while the other of the two spindle nuts of the second drive arrangement is fixed to the middle one of the five column elements, i.e. in particular the third column element. Thus the threaded spindle, which is rotatably mounted (and driven) on the fourth column element, can turn up the corresponding spindle nut—and hence also the fourth column element on the third (middle) column element—while the spindle nut, which is rotatably mounted (and driven) on the fourth column element, can push up the corresponding threaded spindle—and hence the fifth (outermost) column element relative to the fourth column element.

In a further preferred embodiment, each of the two drive arrangements comprises a motor, for example an electric motor, such as a DC motor with or without brushes. Suitably, the motors form a drive of the respective drive arrangement.

In order, in the case of failure of one of the motors, to avoid an uncontrolled collapse of the lifting column and/or an overload of the motors under heavy load, alternatively or additionally a braking device is provided for limiting a movement speed on movement of the column elements relative to one another.

Each of the two drive arrangements suitably comprises a planetary gear mechanism. Thus a torque exerted by the respective motor can be efficiently adapted, in particular optimized. For example, a rapid rotation of the drive shafts can be converted into a relatively slow translation of the column elements relative to one another, so that even heavy loads can be reliably positioned.

The motor, the braking device and the planetary gear mechanism of a respective drive arrangement are preferably arranged coaxially, i.e. one behind the other along the longitudinal axis of the lifting column. This arrangement is particularly advantageous with respect to a compact lifting column, in that it allows optimum use of installation space within the lifting column.

In a further preferred embodiment, a line arrangement is provided for supplying power to the first and second drive arrangements. Suitably, the line arrangement is at least in part arranged laterally between the first and second drive arrangements, and hence particularly compactly.

The line arrangement preferably comprises a first line portion which runs from a power supply of the lifting column to the first drive arrangement, in particular for driving the first drive arrangement, and at least in part forms a first line loop in at least one operating state of the lifting column, e.g. when the lifting column is retracted. For example, the first line portion, e.g. one or more parallel running cables, may run from a power pack or another (electrical) connection of the lifting column up to the drive of the first drive arrangement such that at least a part of the first line portion hangs down, in any case when the lifting column is retracted. Advantageously, to this extent the second column element may be moved relative to the first column element without the extension being limited by the line arrangement. Suitably, the length of the first line portion for this amounts substantially to at least one-and-a-half times, in particular between one-and-a-half times and twice the length of one of the column elements.

In order for the line arrangement not to limit the extension on movement of the remaining column elements relative to one another, said arrangement preferably comprises a second line portion. The second line portion suitably runs from the first to the second drive arrangement, in particular a drive of the second drive arrangement, and at least in part forms a second line loop in at least one operating state of the lifting column, e.g. when the lifting column is retracted. For example, the second line portion, e.g. one or more cables running in parallel, may run from the drive of the first drive arrangement to the drive of the second drive arrangement such that at least a part of the second line portion hangs down, in any case when the lifting column is retracted. Suitably, the length of the second line portion amounts to at least twice the length of one of the column elements.

The lifting column may be used as a floor stand. In this case, the power supply is suitably arranged at a lower end of the first (innermost) column element. The first line loop accordingly forms a "lower" line loop, and the second line loop forms an "upper" line loop.

The lifting column may also be used as a ceiling-mounted unit. In this case, the power supply is suitably arranged at an upper end of the first (innermost) column element. The second line loop then accordingly forms a "lower" line loop, while the first line loop forms an "upper" line loop.

In order to avoid damage to the line portions and/or be able to laterally reinforce the line portions, the first and/or second line loops are preferably arranged at least in part in a line sheath. The line sheath is suitably formed by multiple sheath segments connected together in a chain. To this extent, this could also be described as a line or cable chain which forms at least part of the first and/or second line portion.

Installation space may be saved if the second line loop is arranged at least partly inside the first line loop (when the lifting column is used as a floor stand), or vice versa (when the lifting column is ceiling-mounted) in at least one operating state of the lift column, e.g. when the lifting column is retracted. In other words, in this operating state, the lower line loop may run at least in part around the upper line loop.

In a further preferred embodiment, a plurality of first slide elements is provided which are arranged on the outsides of all four innermost column elements so as to slide on an inside of the respective next outer column element. For example, first slide elements may be arranged on an outside of the first, second, third and fourth column elements so as to be able to slide on the inside of the second, third, fourth and fifth column elements.

Alternatively or additionally, a plurality of second slide elements may be provided which are arranged on the insides of all four outermost column elements so as to slide on an outside of the respective next inner column element. For example, second slide elements may be arranged on an inside of the fifth, fourth, third and second column elements so as to be able to slide on the outside of the fourth, third, second, and first column elements.

In comparison with conventional roller-based solutions, the lifting column with first and/or second slide elements can be made more compact in cross-section. The provision of both first and second slide elements may prevent tilting of the column elements, in particular if the first and second slide elements are arranged at opposite ends of the column elements.

In a further preferred embodiment, the first and second drive arrangements are formed substantially identically. This can considerably simplify assembly of the lifting column and has significant advantages with respect to procurement and storage of components and spare parts.

In a further preferred embodiment, the lifting column comprises a force sensor for detecting a force exerted on one of the column elements. The lifting column is here configured to control the first and/or second drive arrangement, in particular the motor of the first and/or second drive arrangement, on the basis of the detected force. To this end, the lifting column may for example have a control device. With a lifting column configured in this fashion, the column elements can be guided particularly intuitively.

A second aspect of the invention concerns an X-ray system with an X-ray source, an X-ray detector and a lifting column according to the first aspect of the invention. The X-ray source or the X-ray detector is suitably mounted on the lifting column. By means of the lifting column, the components of the system can be positioned close to a ceiling or floor. This facilitates for example the laying of a patient on the X-ray detector (which may be integrated in a table). At the same time, the components can be moved precisely relative to one another, irrespective of whether they are pulled or pushed for positioning purposes.

As an alternative to the use in an X-ray system, the lifting column according to the first aspect of the invention may also be used in automation systems, i.e. as part of one or more robots. It is also conceivable to use the lifting column in a goods or persons lift which may be mobile.

The invention is explained in more detail below with reference to figures. Where suitable, elements with the same function carry the same reference signs. The invention is not restricted to the exemplary embodiments illustrated in the figures, also not with respect to functional features. The above description and the following description of the figures contain numerous features which are partially combined in the dependent subclaims. These features, like all other features disclosed above and in the following description of the figures, may also be considered individually by the person skilled in the art or combined into suitable further combinations. In particular, all cited features, individually and in any suitable combination, may be combined with the lifting column according to the first aspect of the invention and the X-ray system according to the second aspect of the invention.

The drawings show, at least in part schematically:

BRIEF DESCRIPTION OF THE FIGURES

FIG. 1 an example of a lifting column in a retracted state;
FIG. 3 a cross-section of the lifting column from FIG. 1.

DETAILED DESCRIPTION OF THE INVENTION

Figure 2:
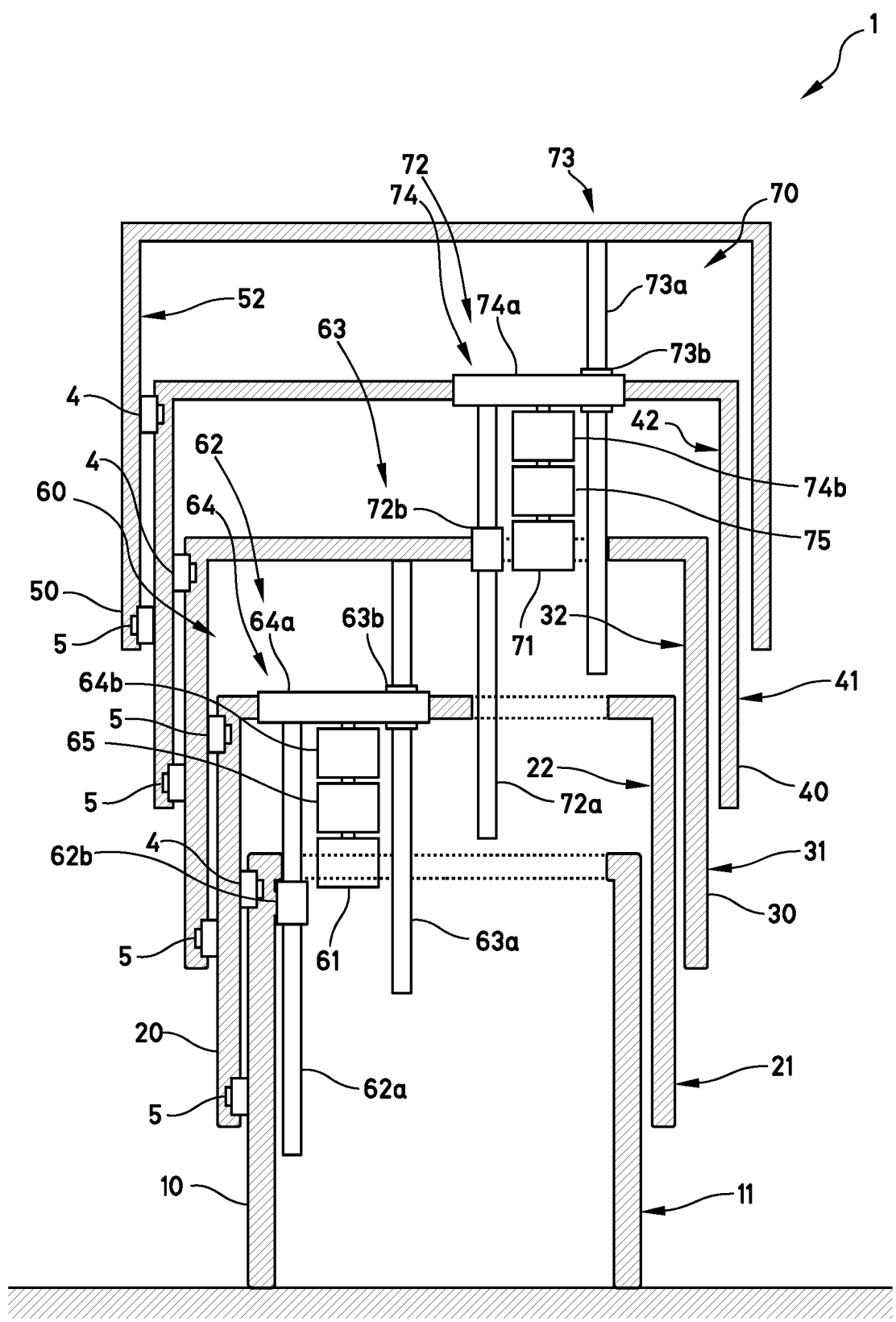
FIG. 2 the lifting column from FIG. 1 in an extended state.

FIG. 1 shows an example of a lifting column 1 in a retracted state. The lifting column 1 has five column elements 10, 20, 30, 40, 50 which are at least partly nested, and a first drive arrangement 60 and a second drive arrangement 70. The first drive arrangement 60 is configured to move the three innermost column elements 10, 20, 30—which are sometimes also referred to below as the first, second and third column elements—relative to one another. The second drive arrangement 70 is configured to move the three outermost column elements 30, 40, 50—which are sometimes also referred to below as the third, fourth and fifth column elements—relative to one another.

To this end, the first drive arrangement 60 preferably comprises a drive 61 and two screw gears 62, 63, each with a threaded spindle 62a, 63a and a spindle nut 62b, 63b. The rotational axes of a drive shaft of the drive 61 and the two screw gears 62, 63 preferably run parallel to one another with a lateral offset. The drive 61 is therefore suitably actively connected via a gear mechanism 64 to screw gears 62, 63, in particular to the threaded spindle 62a of the one screw gear 62 and to the spindle nut 63b of the other screw gear 63.

The spindle nut 62b of the one screw gear 62 is here preferably fixed on the first, i.e. innermost column element 10. By driving the corresponding threaded spindle 62a, the second column element 20 can be raised or lowered relative to the first column element 10.

Furthermore, the threaded spindle 63a of the other screw gear 63 is preferably fixed on the third, i.e. the middle column element 30. By driving the corresponding spindle nut 63b, the third column element 30 can be raised or lowered relative to the second column element 20.

To save installation space, the gear mechanism 64 may comprise a flat gear 64a. In such a flat gear 64a, gearwheels—which are also known as spur gears because of their end position—are arranged intermeshing in one plane and transmit a torque laterally onto the two screw gears 62, 63 of the first drive arrangement 60.

Alternatively or additionally, the gear mechanism 64 may also comprise a planetary gear mechanism 64b in order to adapt a torque from the drive 61. For space reasons, the planetary gear mechanism 64b is preferably arranged coaxially with the drive 61, i.e. such that the drive shaft of the drive 61 and an input and/or output shaft of the planetary gear mechanism 64b have the same rotational axis.

Also, optionally, the first drive arrangement 60 may have a braking device 65 which is preferably configured for limiting a movement speed on movement of the column elements 10, 20, 30 relative to one another. For space reasons, the braking device 65 is also arranged preferably coaxially with the drive 61, and in some cases also with the planetary gear mechanism 64b. A particularly compact arrangement may be achieved if the drive 61, planetary gear mechanism 64b and/or braking device 65 are arranged substantially aligned in the longitudinal direction of the lifting column 1.

Suitably, the second drive arrangement 70 is constructed correspondingly, in particular identically to the first drive arrangement 60. Accordingly, the second drive arrangement 70 may comprise a drive 71, two screw gears 72, 73 each with a threaded spindle 72a, 73a and a spindle nut 72b, 73b, a gear mechanism 74 comprising a flat gear 74a and/or a planetary gear mechanism 74b, and/or a braking device 75. These elements of the second drive arrangement 70 preferably stand in the same active connection to one another as the corresponding elements of the first drive arrangement 60.

Accordingly, the one threaded spindle 72a of the one screw gear 72 is suitably mounted rotatably on the fourth column element 40 and can be driven by the drive 71. This threaded spindle 72a is preferably actively connected to the one spindle nut 72b fixed on the third (middle) column element 30, so that the fourth column element 40 can be raised or lowered relative to the third column element 30.

Similarly, the other spindle nut 73b of the other screw gear 73 is suitably rotatably mounted on the column element 40 and can be driven by the drive 71. This spindle nut 73b is preferably actively connected to the other threaded spindle 73a fixed on the fifth (outermost) column element 50, so that the fifth column element 50 can be raised or lowered relative to the fourth column element 40.

FIG. 2 shows the lifting column 1 from FIG. 1 in an extended state. Because of the coupling of the first and second drive arrangements 60, 70 via the third (middle) column element 30, the travels of the four screw gears 62, 63, 72, 73 are added together so that, even with an axially compact lifting column 1, for example with a height of 600 mm, a greater total extension, e.g. of 2 m or more, can be achieved. The screw gears 62, 63, 72, 73 with the threaded spindles 62a, 63a, 72a, 73a and the spindle nuts 62b, 63b, 72b, 73b can here stabilize the lifting column 1, in particular against both tension and pressure.

FIG. 2 also shows a plurality of first slide elements 4 which are arranged on the outsides 11, 21, 31, 41 of the first, second, third and fourth (the four innermost) column elements 10, 20, 30, 40, so as to slide on a respective opposite inside of the second, third, fourth or fifth (the four outermost) column elements 20, 30, 40, 50. Similarly, a plurality of second slide elements 5 is shown, which are arranged on the insides 22, 32, 42, 52 of the four outermost column elements 20, 30, 40, 50 so as to slide on the respective opposite outsides 11, 21, 31, 41 of the four innermost column elements 10, 20, 30, 40. The provision of slide elements 4, 5 is sufficient to allow the extension or retraction of the lifting column 1 by means of the four screw gears 62, 63, 72, 73. A greater reduction in friction between the column elements 10, 20, 30, 40, 50, for example by means of corresponding rollers as used in conventional lifting columns, is not necessary.

FIG. 3 illustrates a cross-section of the lifting column 1 from FIG. 1, which clearly shows the arrangement of the two drive arrangements 60, 70 in an interior 2 of the lifting column 1, i.e. inside the nested column elements 10, 20, 30, 40, 50. For efficient use of space, the drive arrangements 60, 70 may be arranged laterally offset to one another in a respective half 2a, 2b of the interior 2. Suitably, the drive 61, 71 of the respective drive arrangement 60, 70 is here arranged laterally between the corresponding screw gears 62, 63, 72, 73.

Preferably, a gap 3 is formed between the drive arrangements 60, 70. A line arrangement for supplying power to the first and second drive arrangements 60, 70 may be arranged in this gap 3, as shown in connection with FIG. 4.

Figure 4:
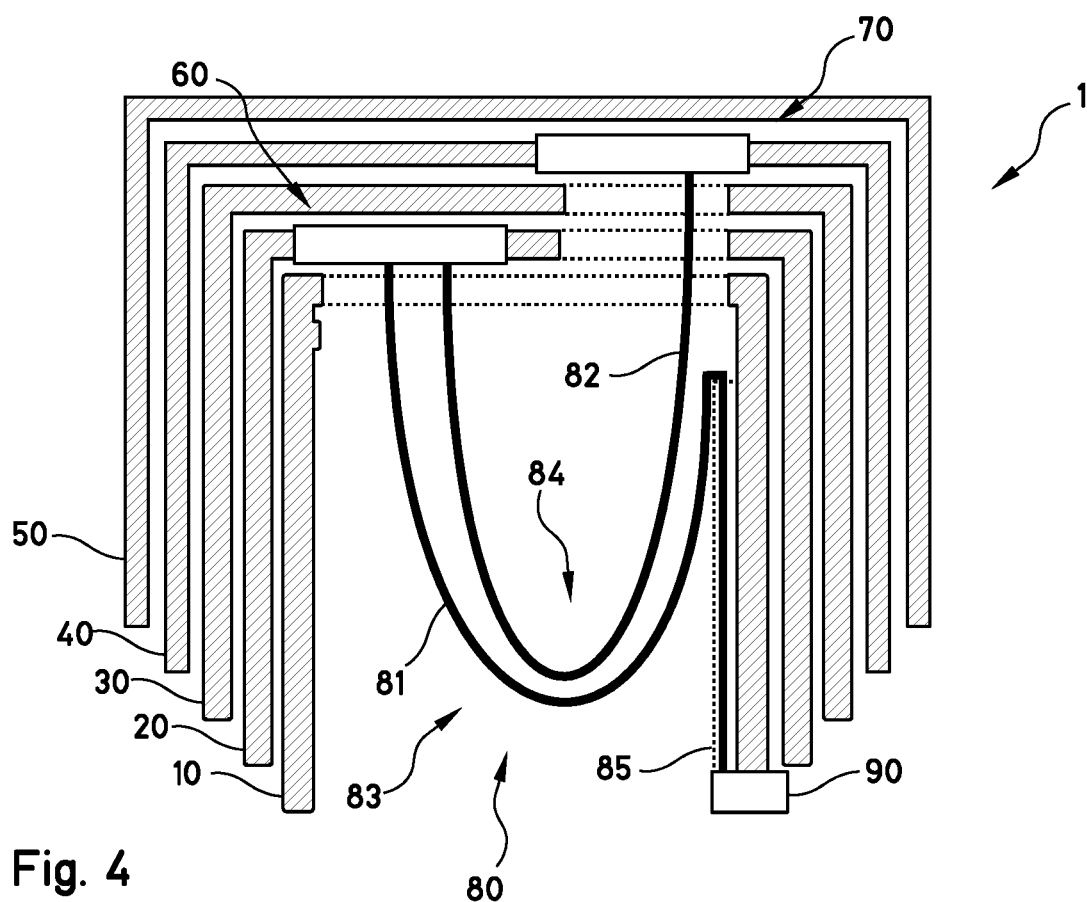
FIG. 4 an example of a line arrangement.

FIG. 4 shows an example of a line arrangement 80 of a lifting column 1. The line arrangement 80 has a first line portion 81, a second line portion 82 and optionally a line guide 85. The first line portion 81 suitably runs between a power supply 90 of the lifting column 1, e.g. a power pack, and a first drive arrangement 60 which is configured to move the three innermost column elements 10, 20, 30 relative to one another. The second line portion 82 suitably runs between the first drive arrangement 60 and a second drive arrangement 70 which is configured to move the three outermost column elements 30, 40, 50.

The line portions 81, 82 are suitably configured such that, at least in part, they form a first lower line loop 83 and a second upper line loop 84 in at least one operating state of the lifting column 1, e.g. in the retracted state shown. This means that the line portions 81, 82 hang down at least in part, whereby the line portions 81, 82 can follow on extension of the lifting column 1.

To this end, the line guide 85 of the first line portion 81 may run along an inside of the first (innermost) column element 10, in particular up to an upper end of the column element 10.

As shown in FIG. 4, the second line portion 82 runs at least partly inside the first lower line loop 83 in at least one operating state. In particular, the second upper line loop 84 is at least partly arranged inside the lower line loop 83. The line portions 81, 82 may be at least partly, in particular in the region of the line loop 83, 84, arranged in a line sheath as shown in FIG. 5.

Figure 5:
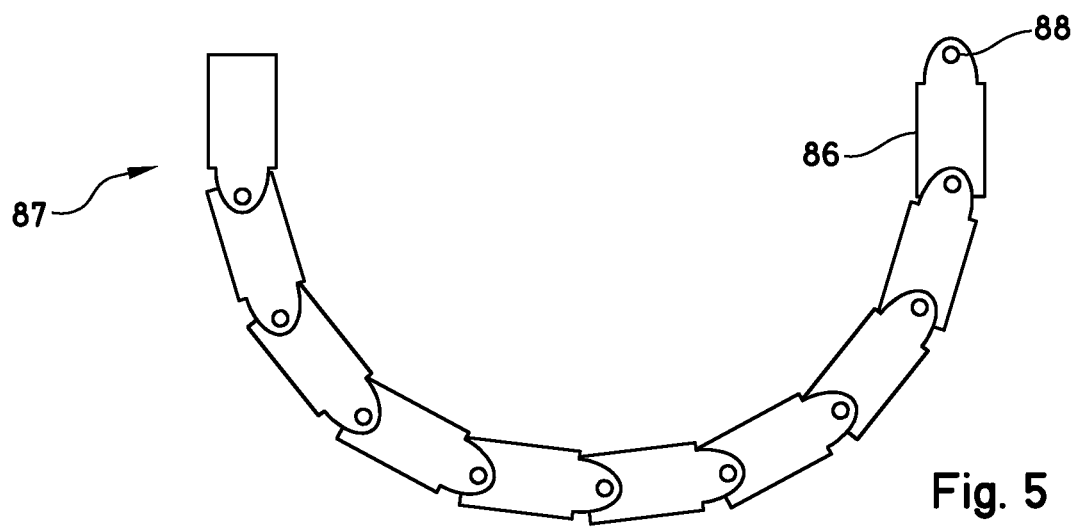
FIG. 5 an example of sheath segments connected together as a chain, and
FIG. 6 an example of an X-ray system.

FIG. 5 shows an example of the sheath segments 86 which are connected together in a chain to form a line sheath 87 for receiving line portions, e.g. one or more cables. The sheath segments 86 (of which, for reasons of clarity, only one carries a reference sign) are suitably connected together at pivot axes 88 (of which again, for reasons of clarity, only one carries a reference sign). The pivot axes 88 run parallel to one another and suitably horizontally. Thus line portions arranged inside the line sleeve 87 may form loops. A lateral movement, i.e. transversely to the figure plane, can thus however be suppressed. To this extent, it is preferred to provide a line sheath 87 for the line portions running in the gap shown in FIG. 3, in order to prevent the line portions from catching in the drive arrangements.

FIG. 6 shows an example of an X-ray system 100 with an X-ray source 110, an X-ray detector 120 and a lifting column 1. Here, the X-ray detector 120 is integrated in a patient table 130 which is mounted so as to be adjustable in height by means of the lifting column 1.

Alternatively or additionally to the arrangement shown in FIG. 6, the X-ray source 110 may also be mounted movably by means of the lifting column 1. To this extent, in general terms, the lifting column 1 may serve as a stand, namely in particular as a floor stand or ceiling-mounted unit.

LIST OF REFERENCE SIGNS

1 Lifting column
2 Interior
2a, 2b Half
3 Gap
4 First slide element
5 Second slide element
10 First (innermost) column element
20 Second column element
30 Third (middle) column element
40 Fourth column element
50 Fifth (outermost) column element
11, 21, 31, 41 Outside
22, 32, 42, 52 Inside
60 First drive arrangement
70 Second drive arrangement
61, 71 Drive
62, 63, 72, 73 Screw gear
62a, 63a, 72a, 73a Threaded spindle
62b, 63b, 72b, 73b Spindle nut
64, 74 Gear mechanism
64a, 74a Flat gear
64b, 74b Planetary gear mechanism
65, 75 Braking device
80 Line arrangement
81 First line portion
82 Second line portion
83 First line loop
84 Second line loop
85 Line guide
86 Sheath segment
87 Line sheath
88 Pivot axis
90 Power supply
100 X-ray system
110 X-ray source
120 X-ray detector
130 Patient table

The invention claimed is:

1. A lifting column comprising:
   at least five column elements being at least partly nested;
   a first drive arrangement configured to move a first group of three column elements of said at least five column elements relative to one another, said first group including an innermost column element of said at least five column elements; and
   a second drive arrangement configured to move a second group of three column elements of said at least five column elements relative to one another, said second group including an outermost column element of said at least five column elements,
   the first group and the second group sharing a shared column element of said at least five column elements;
   each of said drive arrangements including a respective drive and two respective screw gears actively connected to said respective drive, and each of said screw gears having a respective threaded spindle and a respective spindle nut.

2. The lifting column according to claim 1, wherein said shared column element is a middle column element, and said first and second drive arrangements are mechanically coupled together by said middle column element.

3. The lifting column according to claim 1, which further comprises an interior of the lifting column, said interior having two halves, and said first and second drive arrangements being laterally offset relative to one another and each being disposed in a respective one of said halves.

4. The lifting column according to claim 1, wherein each of said drives is configured for driving said threaded spindle of one of said two screw gears actively connected thereto and for driving said spindle nut of another of said two screw gears actively connected thereto.

5. The lifting column according to claim 1, which further comprises gear mechanisms, each of said drives having a respective drive shaft actively connected by a respective one of said gear mechanisms to a respective one of said screw gears of a respective one of said drive arrangements being laterally offset relative to said respective drive shaft.

6. The lifting column according to claim 1, wherein:
   said drive of said first drive arrangement is fixed to a first group middle column element of said first group; and
   said drive of said second drive arrangement is fixed to a second group middle column element of said second group.

7. The lifting column according to claim 6, wherein:
   said at least five column elements include a center column element;
   one of said threaded spindles and one of said spindle nuts of said first drive arrangement are mounted rotatably on said first group middle column element, another of said threaded spindles of said first drive arrangement is fixed to said center column element, and another of said spindle nuts of said first drive arrangement is fixed to said innermost column element and
   one of said threaded spindles and one of said spindle nuts of said second drive arrangement are mounted rotatably on said second group middle column element, another of said threaded spindles of said second drive arrangement is fixed to said outermost column element, and another of said spindle nuts of said second drive arrangement is fixed to said center column element.

8. The lifting column according to claim 1, wherein each of said first and second drive arrangements includes:
   a motor;
   a braking device for limiting a movement speed upon movement of said column elements relative to one another; and
   a planetary gear mechanism;
   said motor, said braking device and said planetary gear mechanism being disposed coaxially.

9. The lifting column according to claim 1, wherein:
   a plurality of first slide elements respectively disposed on the outsides of four column elements so as to slide on an inside of a respective neighboring column element; and
   a plurality of second slide elements respectively disposed on the insides of four column elements so as to slide on an outside of a respective neighboring column element.

10. The lifting column according to claim 1, wherein said first and second drive arrangements are structurally identical.

11. The lifting column according to claim 1, which further comprises a force sensor for detecting a force exerted on one of said column elements, permitting the lifting column to control at least one of said first or second drive arrangements on a basis of a detected force.

12. A lifting column comprising:
at least five column elements being at least partly nested;
a first drive arrangement configured to move a first group of three column elements of said at least five column elements relative to one another, said first group including an innermost column element of said at least five column elements; and
a second drive arrangement configured to move a second group of three column elements of said at least five column elements relative to one another, said second group including an outermost column element of said at least five column elements;
the first group and the second group sharing a column element of said at least five column elements;
a power supply for supplying power to said first and second drive arrangements; and
a line arrangement including a first line portion running from said power supply to said first drive arrangement and a second line portion running from said first drive arrangement to said second drive arrangement.

13. The lifting column according to claim 12, which further comprises:
line sheaths each defined by respective multiple sheath segments connected together in a chain, said first line portion at least in part defining a first line loop in at least one operating state of the lifting column; and
said second line portion at least in part defining a second line loop in at least one operating state of the lifting column; and
said first and second line loops each being disposed at least in part in a respective one of said line sheaths.

14. The lifting column according to claim 13, wherein said second line loop is disposed at least in part inside said first line loop, or said first line loop is disposed at least in part inside said second line loop, in at least one operating state of the lifting column.

15. A lifting column comprising:
five column elements being at least partly nested;
a first drive arrangement configured to move a first group of three column elements of said five column elements relative to one another; and
a second drive arrangement configured to move a second group of three column elements of said five column elements relative to one another;
each of said drive arrangements including a respective drive and two respective screw gears actively connected to said respective drive, and each of said screw gears having a respective threaded spindle and a respective spindle nut.

* * * * *